United States Patent [19]

Berger

[11] Patent Number: 4,725,294
[45] Date of Patent: Feb. 16, 1988

[54] APPARATUS FOR COLLECTION OF PARTICULATE MATTER FROM AN AMBIENT GAS

[75] Inventor: Josef Berger, Los Altos, Calif.

[73] Assignee: VLSI Standards, Inc., Mountain View, Calif.

[21] Appl. No.: 25,347

[22] Filed: Mar. 13, 1987

[51] Int. Cl.⁴ .............................................. B01D 53/30
[52] U.S. Cl. ..................................... 55/270; 73/863.22
[58] Field of Search ....................... 55/270, 465, 418; 73/863.22, 864.73, 863.21

[56] References Cited

U.S. PATENT DOCUMENTS

| 982,488 | 1/1911 | Gamble | 55/418 |
|---|---|---|---|
| 3,289,481 | 12/1966 | Barnes | 55/270 |
| 3,343,199 | 9/1967 | Nolte | 55/434 |
| 3,458,974 | 8/1969 | Orr, Jr. et al. | 55/209 |
| 3,518,815 | 7/1970 | McFarland et al. | 73/863.22 |
| 3,711,707 | 1/1973 | Lilienfeld et al. | 250/43.5 |
| 3,970,428 | 7/1976 | Barringer | 23/230 |
| 4,321,822 | 3/1982 | Marple et al. | 55/270 |
| 4,378,159 | 3/1983 | Galbraith | 356/237 |

Primary Examiner—Bernard Nozick
Attorney, Agent, or Firm—Thomas Schneck

[57] ABSTRACT

An apparatus for collecting particulate matter from a test atmosphere including a chamber having internal walls and posts which support an unpatterned ultraclear wafer. A gas inlet tube penetrates the chamber with a central gas passageway for directing a stream of high velocity gas onto the wafer. Particles from the stream of gas are collected across most of the surface of the wafer by impaction and by deposition due to enhanced diffusion provided by a vacuum environment.

13 Claims, 4 Drawing Figures

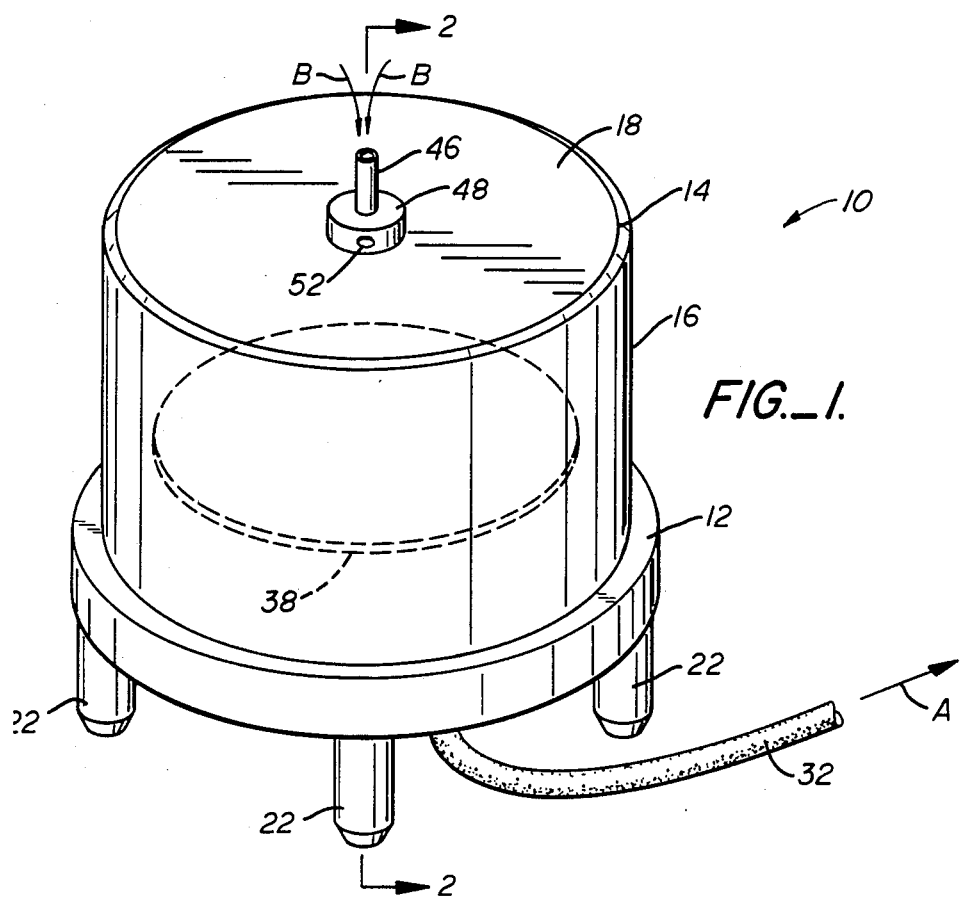
FIG._1.
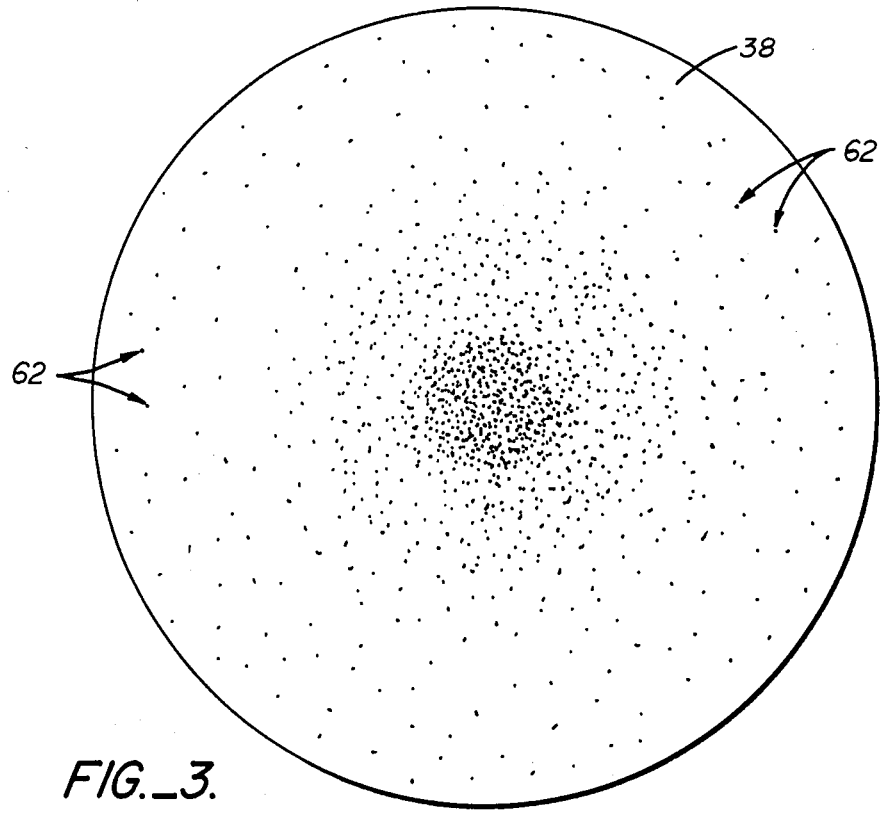
FIG._3.

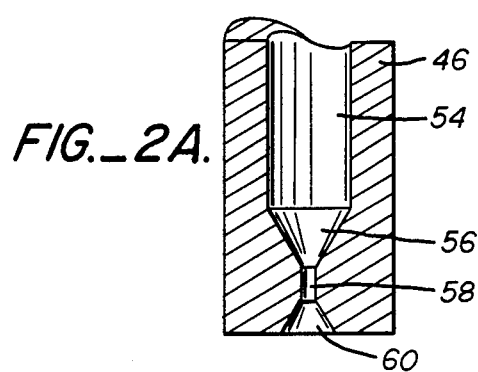
FIG._2A.
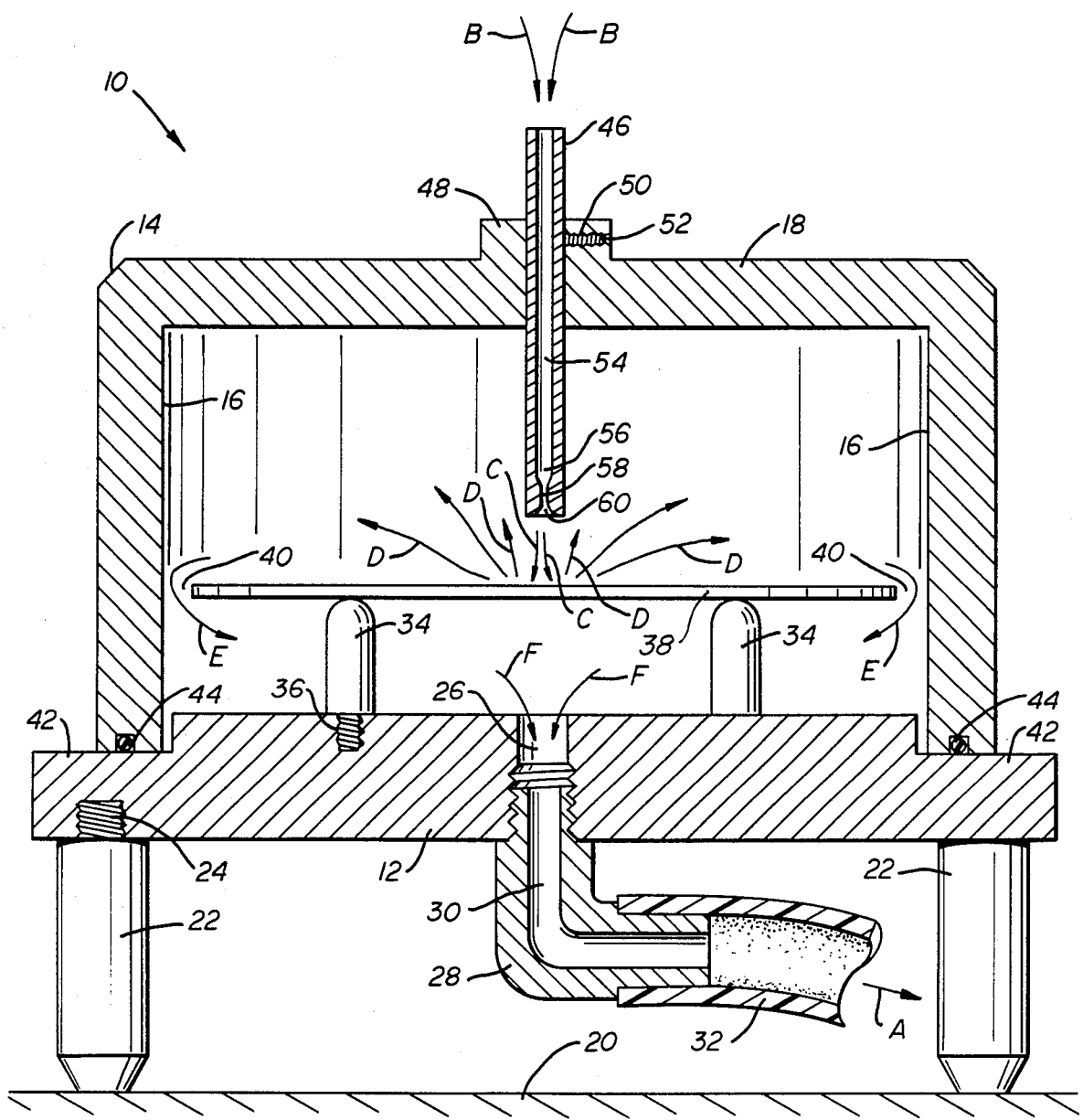
FIG._2.

APPARATUS FOR COLLECTION OF PARTICULATE MATTER FROM AN AMBIENT GAS

TECHNICAL FIELD

The invention relates to air quality testing apparatus and in particular to an apparatus for collecting particulate matter from the atmosphere of a room for particle counting and analysis.

BACKGROUND ART

Semiconductor wafers are shipped to a processing site in a vacuum sealed container. The wafers are then unpacked and processed in clean rooms. Care must be taken since particulate matter on a wafer will flaw or contaminate the wafer and subsequent integrated circuit chips built on the wafer, causing circuit defects and reducing reliability.

Federal and industrial standards have been established for the allowable concentration of particulate matter in the atmosphere of various clean rooms. Both for the purpose of remaining within a particular standard and for the purpose of self-regulating quality control, it is necessary to regularly test the clean room to determine the concentration of particles in the atmosphere.

Devices for collecting particulate matter from an atmosphere are known. U.S. Pat. No. 3,711,707 to Lilienfeld et al. is typical of the prior art collectors. The patent describes a monitoring apparatus which collects aerosol particles by impaction. Particle impactors operate under the principle that as an air stream is caused to strike a substrate, the heavy particles impact upon the surface because of their mass.

U.S. Pat. No. 3,970,428 to Barringer operates in much the same manner as particle impactors. The substrate, however, is replaced by a strip of tape having an adhesive coating to capture the particles. The strip of tape is advanced periodically so that the particulate matter is collected in a number of "dots" or circular areas. U.S. Pat. No. 3,458,974 to Orr, Jr., et al. describes a collector which captures particles by impinging a heated gas on a cooled surface. The temperature gradient causes the particulate matter to be driven toward the cooler surface by thermal forces, whereupon the particles are collected.

Conventional prior art collectors and detectors operate only where relatively high concentrations of particles or relatively heavy particles are encountered. Additionally, some conventional devices require the substrate to be mechanically fastened to the devices. Mechanical fastening may cause particulate matter to enter the atmosphere.

Some impactors center the collected particles in one small area, thereby making it more difficult to determine the size of individual particles. Barringer and Orr, Jr., et al. solve this problem by moving the tape or substrate, but the particulate matter is still collected only where the air stream is directed.

It is an object of the present invention to provide an apparatus for collecting particulate matter from an ambient atmosphere that is capable of collecting matter smaller than that collected by conventional impactors and is able to provide a suitable measurement surface. A further object is to standardize the gas flow rate in such an apparatus despite fluctuations of pressure from a vacuum source, thereby making data from testing as a function of time more reliable.

DISCLOSURE OF THE INVENTION

The above objects have been achieved by an apparatus which collects particulate matter from an ambient gas initially by impaction but also by deposition of matter resulting from gravitational force, an extended mean free path and an enhanced diffusion pattern. A turbulent stream of gas from the test atmosphere is directed at a removable ultraclean nonporous substrate and the larger particles within the stream will be impacted onto the substrate. The stream of gas is diffused radially outwardly, being provided entry to a low pressure housing for an extended mean free path for the gas molecules, lengthening Brownian movement, yet allowing van der Waals forces to collect particulate matter from the stream of gas at a nearby collection surface. Particulate matter from the gas stream is distributed across the surface of the substrate, rather than being grouped in a small area. Thus, it is possible to subsequently read the substrate to determine not only the amount of the particulate matter in the atmosphere of a given area, but also the size of the particles, using an appropriate readout device.

The housing includes a chamber having a body portion, consisting mainly of a floor with upright support posts and a dome shaped closure over the floor consisting mainly of a cylindrical side wall and a lid portion. The dome shaped closure is removable to permit access to the inside chamber. Within the evacuable chamber the support posts, having rounded upper surfaces, define a horizontal support plane. In the center of the body portion is a vacuum port that is in fluid communication with a vacuum pump for the evacuation of gas from the chamber.

An ultraclean, nonporous substrate is positioned atop the support posts. Preferably, the substrate is a silicon wafer that extends along a horizontal plane when positioned atop the support posts. New silicon and similar wafers, packaged by suppliers of wafers to the semiconductor industry, are able to achieve ultraclean surfaces, perhaps the cleanest surfaces known to man. For this reason we have selected such wafers as a test substrate regardless of the ambient gas environment. Thus, for biological laboratories, optics laboratories and the like, new semiconductor wafers would still be used as a test substrate in the invention.

A gas inlet tube penetrates the lid portion and extends downwardly into the evacuation chamber. When gas is evacuated from the chamber, a stream of gas will be pulled through a center bore in the inlet tube to direct the stream onto the substrate for impaction of particles. Typically the stream of gas is directed at the center of the substrate. The center bore of the inlet tube has a non-uniform narrow width to regulate the gas flow rate to the chamber. The non-uniform shape of the inlet tube induces turbulence to a stream of gas passing therethrough. While the stream of gas continues to have an axial component of motion, the rapid radial change in direction and velocity produce an areawise spreading of particles. A flared exit end of the center bore diffuses the turbulent stream to avoid a dense hit area at the center of the substrate. The distance between the flared exit and the substrate is determinative of the particle diffusion.

A peripheral gas passageway exists between the circumference of the substrate and the cylindrical side wall of the chamber. Thus, evacuation of gas in the chamber will diffuse the stream of gas from the inlet tube radially outwardly after impaction upon the substrate. Particulate matter from the stream will collect on the surface of the substrate by gravitational pull and by van der Waals attraction. In this manner the larger particles will be collected near the center of the substrate, while increasingly small particles will be collected as the circumference of the substrate is neared. After the gas has passed over the wafer for a predetermined time, the wafer is removed from the housing and is scanned by a particle surface scanner, such as the detector disclosed in U.S. Pat. No. 4,378,159 to Galbraith.

An advantage of the present invention is that it is possible to obtain a particle count as well as an indication of the distribution and size of particles over the wafer surface using a scanner of the type mentioned above. The invention is not limited to detection of particles having a mass sufficiently great to be impacted during an initial impingement. Another advantage is that the lid portion is secured to the body portion by vacuum. Thus, there is no need for any mechanical fastening which would supply particulate matter to the atmosphere. A third advantage is that the inlet tube regulates the gas flow rate to the evacuation chamber so that the gas flow rate remains relatively constant despite fluctuations in pressure by the vacuum source. Data acquired from testing as a function of time is thereby rendered more reliable. Moreover, the turbulence of the stream of gas induced by the inlet tube causes particle dispersion across the substrate.

BRIEF DESCRIPTION OF THE DRAWINGS

FIG. 1 is a perspective plan view of a particle collection apparatus in accord with the present invention.

FIG. 2 is a side sectional view of the apparatus of FIG. 1 taken along lines 2—2.

FIG. 2A is an enlarged view of the inlet tube of FIG. 2.

FIG. 3 is a top elevational view of the substrate of FIG. 2.

BEST MODE FOR CARRYING OUT THE INVENTION

With reference to FIGS. 1 and 2, a particle collector 10 includes a housing having a chamber body 12 and a lid portion 14. The lid portion includes a cylindrical side wall 16 and a cover 18 which, together with the chamber body 12 form an evacuation chamber.

The particle collector 10 is supported above a surface 20 by a plurality of legs 22 that are fastened to the chamber body 12 by threaded bolts 24. The chamber body has a center vacuum port 26 that is at least partially internally threaded. An elbowed fitting 28 is air-tightly secured to chamber body at the center vacuum port 26. The elbow fitting 28 has a 0.5 inch diameter bore 30 and is in fluid communication with a vacuum source, not shown, by means of a vacuum hose 32.

A number of support posts 34 having dome-shaped upper extremities are fastened to the body chamber 12 by threaded bolts 36. The support posts 34 are preferably one inch in height. The body chamber is constructed of aluminum, has a circumference of approximately eight inches, and is supported above the surface 20 by approximately two inches.

Removably positioned atop the support posts 34 is an ultraclean nonporous substrate 38. Preferably, the substrate 38 is an unpatterned silicon wafer, preferably a new, vacuum packed wafer manufactured for fabrication of semiconductor integrated circuits. A new wafer is utilized in the present invention since the wafer provides the cleanest surface available. While there are many techniques for cleaning wafers, the best techniques are secret, known only to manufacturers of wafers for the semiconductor industry. The silicon wafer 38 is positioned so that the wafer is concentric with the vacuum port 26.

The inner circumference of the cylindrical side wall 16 is greater than the circumference of the silicon wafer 38 so that a periphery gas passageway 40 exists between the side wall and the wafer. The internal diameter of the evacuation chamber is typically slightly more than six inches, but the preferred diameter is dependent upon the diameter of the wafer. The internal chamber diameter is selected to accommodate four to eight inch wafers. The side wall 16 rests on a lipped portion 42 of the chamber body 12. The side wall, and therefore the entire lid portion 14, is held to the chamber body in air-tight relation by evacuation force. An O-ring 44 aids in sealing the side wall to the chamber body. Thus, the particle collector 10 requires no mechanical fastening during either insertion or removal of a test silicon wafer.

A gas inlet tube 46 is slidably fit through a step protrusion 48 in the cover 18 of the lid portion. The inlet tube 46 is selectively positioned by means of a set screw 50 disposed in an internally threaded hole 52 of the step protrusion 48. Preferably, the inlet tube will extend into the evacuation chamber a distance of one and one-half inches, to be positioned in the range of approximately one-half inch to one inch above the silicon wafer 38.

Referring now to FIGS. 2 and 2A, the gas inlet tube 46 includes a center gas passageway having a first, relatively wide segment 54 that leads to a funnel segment 56. The molecules of a stream of gas will be accelerated as the area of the inlet tube gas passageway is reduced. The funnel segment 56 of the gas passageway terminates at an alignment segment 58. The diameter of the gas passageway at the alignment segment 58 is approximately 0.020 inches.

The alignment segment 58 of the inlet tube 46 is the narrowest passage for a stream of gas passing through the particle collector 10. Thus, it is the diameter of the alignment segment 58 which determines the maximum velocity of the molecules of gas for a given evacuation pressure. The flow of gas through the inlet tube is at a high velocity. The motion of the stream of gas is in the axial direction of the inlet tube but turbulence is induced by the inlet tube. The rapid radial changes in direction and velocity provide an areawise spreading of particles. Prior to deposition upon the substrate 38 a stream of gas progressing through the inlet tube is fanned slightly by a flared segment 60. The flared segment avoids the dense hit area of particle collection that normally is associated with collection by impaction. The distance from the inlet tube to the wafer 38 determines the extent of diffusion. Preferably this distance is in the range of 0.5 inches to one inch. The inlet tube is typically constructed of brass, while the lid portion is made of aluminum.

In operation, a vacuum source, not shown, is utilized to evacuate the gas from the evacuation chamber of the particle collector 10. Evacuation of the gas is indicated by Arrow A. As a result a stream of gas, shown by Arrows B, is drawn from the ambient atmosphere and enters the inlet tube 46. Typically the ambient atmosphere is the air of a wafer processing or test clean room, but the particle collector is not limited to this application.

As the molecules of the stream of gas progress through the inlet tube 46, the molecules are accelerated into the alignment segment 58. The diameter of the alignment segment is approximately 0.020 inches. This diameter is important since the alignment segment is determinative of the velocity and turbulence at which gas molecules and particulate matter will strike the silicon wafer 38. That is, given a specific air evacuation rate, the diameter of the alignment segment will define the mass of a particle that is required for collection by the process of impaction and will induce turbulence. Additionally, it has been discovered that the interaction of the geometry of the present invention and the 0.020 inch diameter of the alignment segment provide more reliable data for time testing of particulate matter in a clean room. Typically, pressure for the evacuation of air is provided by the house vacuum at a processing facility. The air evacuation of house vacuum will change somewhat over a period of time, depending upon use of the house vacuum for other purposes. If the change of pressure from the house vacuum affects the flow rate through the evacuation chamber of an impactor, the data provided for determining particle collection during a specified time and flow rate is rendered less reliable. The diameter of the alignment segment 58 through the inlet tube 46, however, stabilizes the flow rate through the evacuation chamber after a pressure differential of 15 inches Hg is reached. House vacuum normally has a pressure differential of 25 inches Hg. and is unlikely to drop below the level of 15 inches Hg. The importance of the diameter of the passageway through the inlet tube is reduced only where the importance of exacting data or the importance of time testing is reduced.

Immediately prior to exit from the inlet tube 46, the turbulent stream of gas is diffused by the flared segment 60. As noted above, the flared segment avoids the dense concentration of impacted particles that is normally associated with collection by impaction. Referring to FIG. 3, a concentration of heavy particles 62 impacted onto the silicon wafer 38 is still collected at the center region of the wafer, but the concentration is over a wider region than would be the case if the flared region 60 were not present. This enhanced diffusion permits acquisition of a significant amount of data concerning the amount and the size of particulate matter collected in the center region.

In FIG. 2, Arrows C indicate the path followed by the stream of gas and the particulate matter in the stream during impacting. The molecules of the gas stream and the particules which are not impacted into the silicon wafer 38 are thereafter diffused upwardly and radially outwardly from the center region of the wafer, as shown by Arrows D. The particulate matter will undergo Brownian movement, colliding with the molecules of the gas and colliding with various walls including side walls 16. The gas molecules will, in a short time, be forced through the periphery gas passageway and then out of the evacuation chamber, as indicated by Arrows E and F, but gravitational pull and van der Waals attraction will cause a significant percentage of any particulate matter to fall out of the stream of gas for collection across the surface of the wafer.

The force of gravity will cause some particles to be collected on the wafer surface. Heavier particles will be collected nearer to the center region of a wafer, as is evidenced by data illustrated in FIG. 3. Less heavy particles are collected nearer the edge of the wafer. Van der Waals attraction causes settled particles to be held on the wafer surface by the attraction between molecules of the ultraclean surface of the silicon wafer 38 and the molecules of the particle.

Van der Waals attraction will also aid in collecting particles which are deflected onto the surface of the silicon wafer after collision with a gas molecule or the side wall 16. The geometry of the evacuation chamber is such that diffusion of particles over the collection surface is enhanced.

After the air from a clean room has passed over the silicon wafer 38 for a predetermined time, the substrate is removed from the housing and is scanned by a particle surface scanner of the type shown in U.S. Pat. No. 4,378,159 to Galbraith. When read by a scanner, the silicon wafer is capable of providing a particle count as well as an indication of the size of any particulate matter in the atmosphere.

FIG. 3 illustrates a wafer 38 which was removed from a particle collector 10 after fifty hours in the furnace loading area of a clean room. The operating time is recorded in order to determine the concentration of particulate matter as a function of time. The heavier particles 62 are impacted in the center of the wafer 38. Lighter particles are deposited closer to the edge of the wafer.

The present invention has been discussed in reference to a clean room wherein semiconductor wafers are processed. While the apparatus was designed specifically for such an application, it is understood that the apparatus may be used in other applications, such as with gas supply lines, process piping and certain ducts, where it is necessary to determine the amount and the size of particulate matter in an atmosphere.

I claim:

1. Apparatus for collecting microscopic particulate matter from a test atmosphere comprising,
a closed evacuable chamber having a body portion and a lid portion, said chamber having interior walls including a side wall, a floor and a ceiling,
support means disposed within said chamber for supporting a substrate,
a nonporous substrate positioned on said support means in spaced apart relation to said chamber ceiling, said substrate having a substantially planar disk shape and having a periphery less than the lateral periphery of said chamber, said substrate extending along a substantially horizontal plane and having an upper surface and a lower surface,
gas inlet means for directing a stream of gas from the exterior of the housing for impingement upon said upper surface of the substrate, said gas inlet means being an inlet tube penetrating said lid portion of said housing, said inlet tube having a hollow center bore directed at substantially the center of said substrate, said inlet tube being spaced apart from said substrate by a distance less than the distance between said substrate and said chamber ceiling, at least a portion of said inlet tube having an interior wall diameter in the range of 0.015 inches and 0.025 inches and said bore having an outwardly flared outlet portion, whereby said inlet tube induces turbulence to a stream of gas progressing therethrough, and vacuum port means disposed below the level of said plane upon which the substrate extends for directing a stream of gas from the interior of the housing to the exterior thereof.

2. The apparatus of claim 1 wherein said vacuum port means provides a pressure differential between the interior and exterior of the housing of at least one-half of an atmosphere of pressure between the interior and exterior of the chamber.

3. The apparatus of claim 1 wherein said evacuable chamber is at least partially cylindrical in shape, having an internal diameter greater than the diameter of said substrate to form a peripheral gas passageway between the circumferential periphery of the substrate and the side wall of the housing.

4. The apparatus of claim 1 wherein said inlet tube bore, said substrate and said vacuum port are substantially concentric.

5. The apparatus of claim 1 wherein said support means is a plurality of upright posts having dome-shaped upper surfaces, said substrate supported atop said dome-shaped upper surfaces of the posts.

6. The apparatus of claim 1 wherein said substrate is an unpatterned semiconductor wafer.

7. The apparatus of claim 2 wherein said wafer has a diameter in the range of four to eight inches.

8. Apparatus for collecting microscopic particles from a test atmosphere comprising, a closed evacuable chamber, at least a portion of said chamber interior having a cylindrical side wall configuration, a support means for supporting a substrate within said chamber, a removable nonporous wafer supported substantially horizontally atop said support means, said wafer having a diameter less than the diameter of said cylindrical side wall, gas inlet means penetrating said chamber for directing a high velocity stream of gas toward the center of said wafer, wherein said gas inlet means is an inlet tube having a hollow center bore, at least a portion of said bore having a diameter in the range of 0.015 inches and 0.025 inches and an outwardly flared outlet portion, whereby the inlet tube induces turbulence to a stream of gas progressing therethrough, and vacuum port means associated with said chamber for evacuating gas from said chamber distal to the gas inlet means, whereby said stream of gas is diffused radially outwardly after direction toward the wafer.

9. The apparatus of claim 8 wherein said wafer is an unpattened silicon wafer.

10. The apparatus of claim 8 wherein said vacuum port means provides a pressure differential of at least one-half of an atmosphere of pressure between the interior and exterior of the chamber.

11. The apparatus of claim 8 wherein said inlet tube, said wafer and said vacuum port are substantially concentric.

12. Apparatus for collecting microscopic particles from a test atmosphere comprising, a chamber having a floor with a plurality of upright posts extending from the floor and a dome shaped closure over the floor in vacuum tight relation with the floor, said posts having free ends defining a horizontal sample collection plane, gas inlet means penetrating said dome shaped closure for directing a gas stream centrally onto said sample collection plane, wherein said gas inlet means is an inlet tube having a hollow center bore, at least a portion of said bore having a diameter in the range of 0.015 inches and 0.025 inches and an outwardly flared outlet portion, whereby the inlet tube induces turbulence to a stream of gas progressing through said inlet tube, vacuum port means associatd with said chamber for evacuating gas from said chamber distal to the gas inlet means, and an ultraclean nonporous semiconductor wafer supported on said posts in the sample collection plane.

13. The apparatus of claim 12 wherein said wafer is an unpatterned wafer having a diameter in the range of four to six inches.

* * * * *